US009675313B2

(12) United States Patent
Kim

(10) Patent No.: US 9,675,313 B2
(45) Date of Patent: Jun. 13, 2017

(54) METHOD FOR DENSITOMETRIC ANALYSIS OF COMPUTED TOMOGRAPHY IMAGE

(71) Applicant: Korea University Research and Business Foundation, Seoul (KR)

(72) Inventor: Dong-Joo Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 137 days.

(21) Appl. No.: 14/838,757

(22) Filed: Aug. 28, 2015

(65) Prior Publication Data

US 2016/0058408 A1    Mar. 3, 2016

(30) Foreign Application Priority Data

Aug. 29, 2014    (KR) ........................ 10-2014-0114541

(51) Int. Cl.
*G06K 9/00*    (2006.01)
*A61B 6/00*    (2006.01)
(Continued)

(52) U.S. Cl.
CPC ............ *A61B 6/5217* (2013.01); *A61B 6/032* (2013.01); *A61B 6/501* (2013.01); *A61B 6/505* (2013.01); *A61B 6/506* (2013.01); *A61B 6/5258* (2013.01); *G06T 5/005* (2013.01); *G06T 7/11* (2017.01); *G06T 7/136* (2017.01); *G06T 7/187* (2017.01); *G06T 11/008* (2013.01);
(Continued)

(58) Field of Classification Search
CPC . G06T 7/187; G06T 7/136; G06T 7/11; G06T 5/005; G06T 5/0012; G06T 11/008; G06T 2207/30016; G06T 2207/10081; G06T 2210/41; A61B 6/5205; A61B 6/506; A61B 6/505; A61B 6/5217; A61B 6/5258; A61B 6/501; A61B 6/032
See application file for complete search history.

(56) References Cited

U.S. PATENT DOCUMENTS

| | | | | |
|---|---|---|---|---|
| 7,031,426 | B2* | 4/2006 | Iatrou | ............... A61B 5/02007 378/18 |
| 2004/0210135 | A1* | 10/2004 | Hynynen | ................ A61B 8/06 600/439 |
| 2010/0130848 | A1* | 5/2010 | Lin | ....................... A61B 5/055 600/410 |

FOREIGN PATENT DOCUMENTS

| | | |
|---|---|---|
| JP | 2005-237441 A | 9/2005 |
| KR | 10-2009-0078665 A | 7/2009 |
| KR | 10-2010-0071595 A | 6/2010 |

OTHER PUBLICATIONS

Reeves, T. E., P. Mah, and W. D. McDavid. "Deriving Hounsfield units using grey levels in cone beam CT: a clinical application." Dentomaxillofacial Radiology (2014).*

* cited by examiner

*Primary Examiner* — Shefali Goradia
(74) *Attorney, Agent, or Firm* — Pearne & Gordon LLP

(57) ABSTRACT

A method for densitometric analysis of a computed tomography image is provided. The method includes converting CT numbers of each pixel of a cross-sectional computed tomography image of the brain into Hounsfield unit (HU) values; eliminating an artifact from the computed tomography image of which the CT numbers of each pixel have been converted into the HU values, and extracting the brain tissues; and extracting a density distribution of the HU values from the computed tomography image, in which the artifact has been removed and the brain tissues have been extracted.

16 Claims, 20 Drawing Sheets

(51) Int. Cl.
    *A61B 6/03*           (2006.01)
    *G06T 11/00*        (2006.01)
    *G06T 5/00*          (2006.01)
    *G06T 7/11*          (2017.01)
    *G06T 7/187*        (2017.01)
    *G06T 7/136*        (2017.01)

(52) U.S. Cl.
    CPC ... *A61B 6/5205* (2013.01); *G06T 2207/10081* (2013.01); *G06T 2207/30016* (2013.01)

FIG. 12
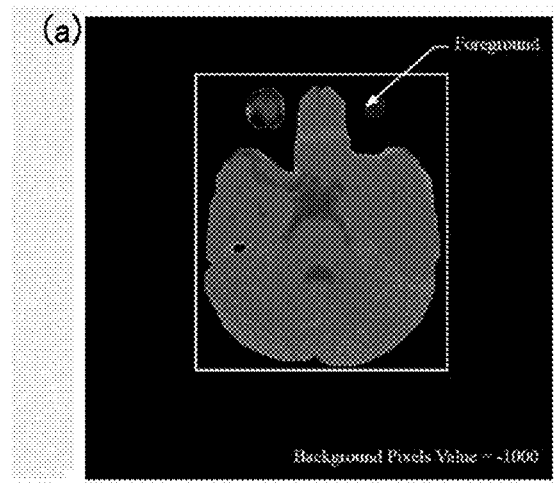
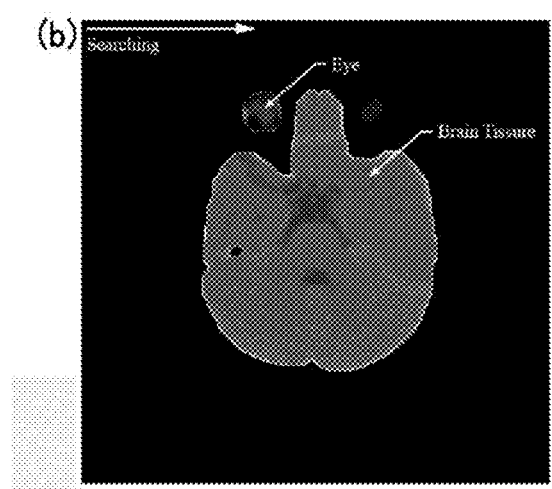
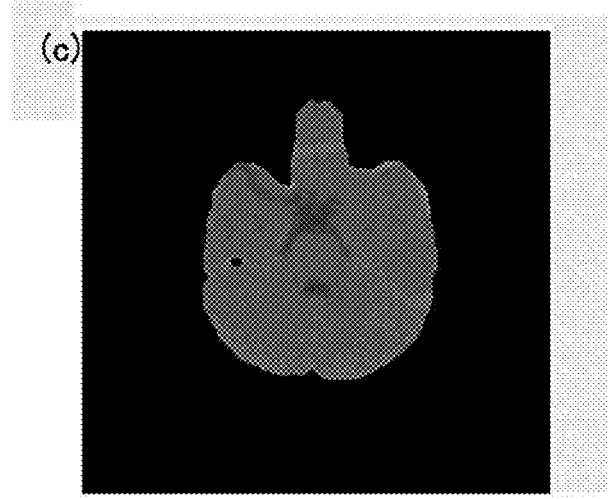

METHOD FOR DENSITOMETRIC ANALYSIS OF COMPUTED TOMOGRAPHY IMAGE

CROSS-REFERENCE TO RELATED APPLICATION

This application claims the benefit of Korea Patent Application No. 10-2014-0114541 filed on Aug. 29, 2014, the disclosures of which are incorporated herein by reference.

TECHNICAL FIELD

The embodiments described herein pertain generally to a method for densitometric analysis of a computed tomography image.

BACKGROUND

Globally, approximately 10 million new patients every year suffer from brain injury, which is likely to become the $3^{rd}$ leading cause of death of human beings by 2020. It is generally known that a primary injury, a direct result of the brain injury, cannot be recovered. However, some studies have reported that most cell death induced by the traumatic brain injury occurs several hours after the initial injury. A typical secondary brain injury is an ischemic injury, which accompanies an increase of the intracranial pressure (ICP) and a decrease of the cerebral perfusion pressure (CPP).

Currently, there are two major medical imaging techniques for evaluating the degree of a brain injury; computed tomography (CT) and magnetic resonance imaging (MRI). The magnetic resonance imaging has higher resolution and sensitivity and, thus, is better able to detect cerebral edema than the computed tomography. However, the magnetic resonance imaging is disadvantageous compared to the computed tomography because it requires longer image acquisition time than the computed tomography and a patient should keep a fixed posture during imaging. For these reasons, it has been reported that the high sensitivity of the magnetic resonance imaging has no significant clinical superiority over the computed tomography, especially for a patient with the traumatic brain injury who requires urgent treatment.

Especially, keeping a fixed posture during the magnetic resonance imaging would be more disadvantageous for pediatric patients. For example, pediatric patients with the brain injury are usually under sedation or general anesthesia before the magnetic resonance imaging as they should keep a fixed posture. The sedation or general anesthesia may cause complications in the heart and the respiratory organs, which may combine with the primary injury and trigger the secondary injury.

On the contrary, the computed tomography may be greatly effective to patients requiring urgent interventions, such as patients with traumatic brain injury or stroke. However, the computed tomography may have high user-dependency whereby the degree of structural abnormality is differently measured according to the observers. Accordingly, as an effort to reduce the user-dependency by standardizing diagnosis of brain injury based on the computed tomography, various classification systems have been suggested. Of those classification systems, Marshall classification that Marshall suggested in 1991 has been the most widely used. Marshall classification is based on six (6) categorizations for traumatic brain injury evaluation depending on the structural abnormalities including a volume of brain lesion, an extent of midline shift, compression of basal cistern, and a presence or absence of surgical interventions. Marshall classification is known to provide critical information on the prognosis of patients with the brain injury. However, Marshal classification still cannot overcome the user-dependency.

Accordingly, there has been a demand for developing a new paradigm for a computed tomography analysis system whereby the limits of the existing analysis system can be overcome.

In this regard, Japanese Patent Laid-open Publication No. 2005-237441 (entitled "Method and Apparatus for Supporting Diagnosis of Brain Disorder") describes a method for providing a more objective diagnosis result for a brain injury, which involves the steps of inputting a brain image of a patient, standardizing the brain image, and, then, carrying out a statistical analysis of the subject brain image by comparing it with a brain image of a normal person.

SUMMARY

In view of the foregoing, example embodiments provide a method for carrying out automated elimination of an artifact from a computed tomography image and, also, a method for conducting a quantitative analysis upon the progression of a lesion.

However, the problems sought to be solved by the present disclosure are not limited to the above description, and other problems can be clearly understood by those skilled in the art from the following description.

In an example embodiment, there is provided a method for densitometric analysis of a computed tomography image is provided. The method includes converting CT numbers of each pixel of a cross-sectional computed tomography image of the brain into Hounsfield unit (HU) values; eliminating an artifact from the computed tomography image of which the CT numbers of each pixel has been converted into the HU values, and extracting the brain tissues; and extracting a density distribution in HU values from the computed tomography images in which the artifact has been removed and the brain tissues have been extracted.

In another aspect of the example embodiments, there is provided a method for calculating a densitometric Hounsfield unit score (DHS) from a computed tomography image. The method includes (a) acquiring one or more computed tomography images of the whole brain; (b) converting CT numbers of each pixel of the computed tomography image into HU values; (c) eliminating an artifact from the computed tomography image of which the CT numbers of each pixel have been converted into the HU values, and extracting the brain tissues; (d) extracting a density distribution in HU values from the computed tomography images in which the artifact has been eliminated and the brain tissues have been extracted; (e) analyzing the density distribution in HU values of the computed tomography images of the whole brain; and (f) calculating the DHS based on a distribution of edema, hemorrhage and normal cells obtained from an analysis result of the density distribution in HU values.

In another example embodiment, there is provided an apparatus for densitometric analysis of a computed tomography image. The apparatus includes a storage device that stores a densitometric analysis application; and a processing unit that configured to interface with the densitometric analysis application, wherein according to execution of the densitometric analysis application, the processing unit converts CT numbers of each pixel of a cross-sectional computed tomography image of the brain into HU values, eliminates an artifact from the computed tomography image of which CT numbers of each pixel has been converted into the HU values and extracting the brain tissues, and then, extracting a density distribution in HU values from the computed tomography images in which the artifact has been eliminated.

In accordance with the example embodiments, an artifact of a computed tomography image can be eliminated automatically by using a fully automated algorithm. Accordingly, the example embodiments have an effect of overcoming the limit of user-dependency of the conventional commercial apparatus for analyzing a brain image.

In addition, unlike conventional classification systems that use one or two sheets of computed tomography images, analysis can be carried out by using computed tomography images of the whole cerebrum according to the example embodiments. Accordingly, the example embodiments have an effect of improving objectivity and clarity of diagnosis by reflecting not only diffuse axonal injury but also change of brain tissues resulting from subarachnoid hemorrhage or ischemia, beyond the limit of local diagnosis.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 12 illustrates an automatic masking process, in the method for densitometric analysis of a computed tomography image in accordance with an example embodiment;

DETAILED DESCRIPTION

Figure 1:
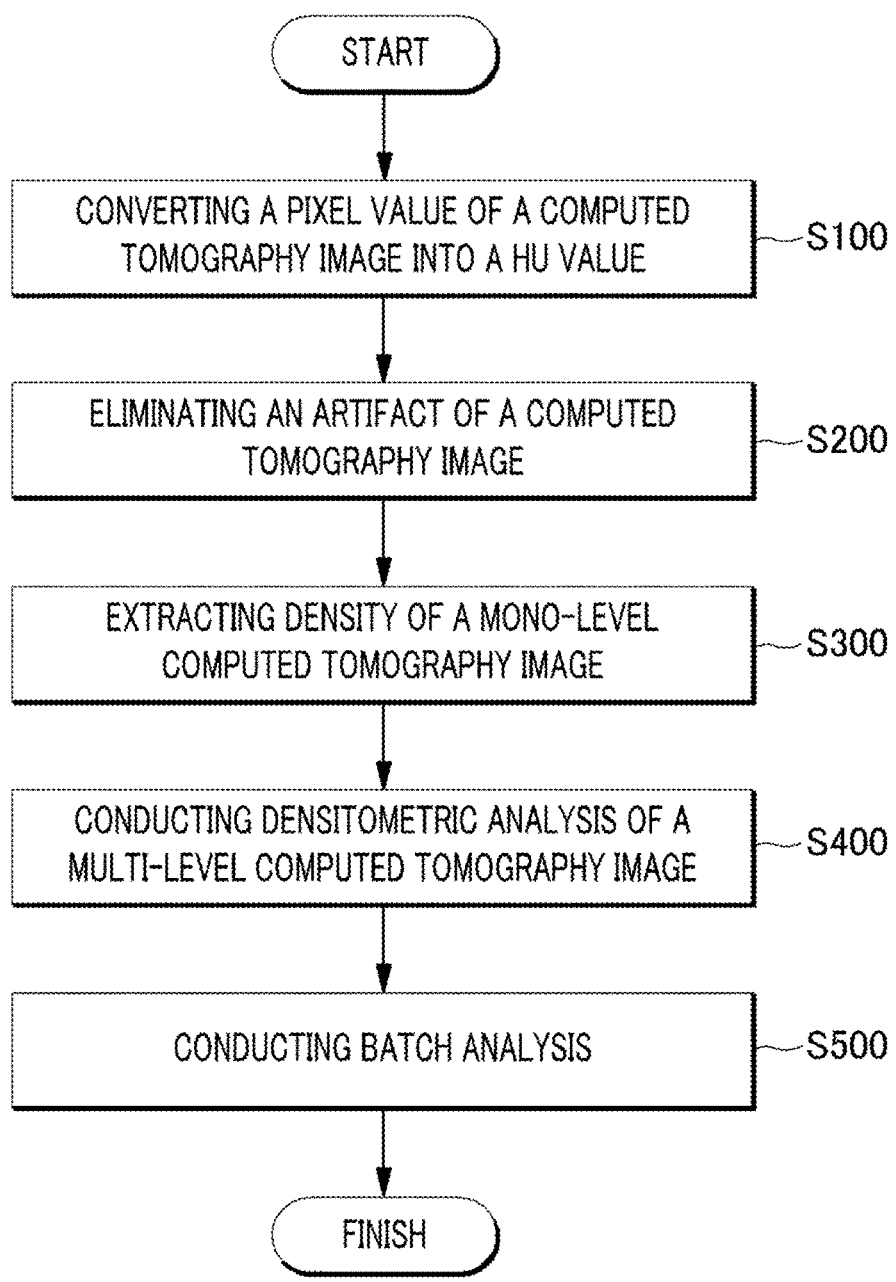
FIG. 1 is a flowchart for describing a method for densitometric analysis of a computed tomography images in accordance with an example embodiment.

Hereinafter, example embodiments will be described in detail with reference to the accompanying drawings so that inventive concept may be readily implemented by those skilled in the art. However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element. Further, the term "comprises or includes" and/or "comprising or including" used in the document means that one or more other components, steps, operations, and/or the existence or addition of elements are not excluded in addition to the described components, steps, operations and/or elements.

In this document, a "unit" includes a unit realized by hardware, a unit realized by software, and a unit realized by both hardware and software. In addition, one (1) unit may be realized by using two (2) or more hardware systems, and two (2) or more units may be realized by one (1) hardware system.

Hereinafter, a method for densitometric analysis of a computed tomography image in accordance with an example embodiment is described in detail with reference to the drawings.

FIG. 1 is a flowchart showing the method for densitometric analysis of a computed tomography image in accordance with an example embodiment.

Figure 2:
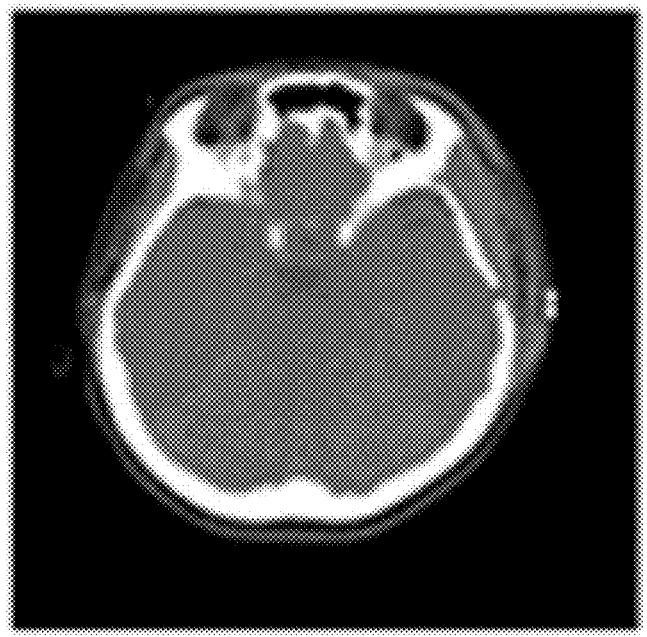
FIG. 2 is an initial computed tomography image, to which the densitometric analysis method in accordance with an example embodiment will be applied.

FIG. 2 shows an initial computed tomography image, to which the densitometric analysis method in accordance with the example embodiment will be applied.

Referring to FIG. 1, the method for densitometric analysis of a computed tomography image may include: converting CT numbers of each pixel of a computed tomography image into HU values (S100); eliminating an artifact of the computed tomography image (S200); extracting a density distribution of a mono-level computed tomography image (S300); conducting densitometric analysis of multi-level computed tomography images (S400); and conducting batch analysis (S500).

First, the step S100 of converting CT numbers of each pixel of a computed tomography image into HU values is a preprocessing for the method for densitometric analysis of a computed tomography image in accordance with the example embodiment. That is, this step S100 is a preparation process to carry out the step S200 of eliminating an artifact of a computed tomography image and the steps S300 and S400 of extracting a density distribution of images. According to an example embodiment, at step S100 of converting CT numbers of each pixel of a computed tomography image into HU values, the computed tomography image is read and pixel information of the computed tomography image is converted into a matrix. Subsequently, a horizontal axis and a center axis of the center of the brain are set by using the pixel information that has been converted into the matrix. In addition, at step S100 of converting CT numbers of each pixel of a computed tomography image into HU values, CT number of a pixel of the computed tomography image is converted into a HU value.

Figure 3:
FIG. 3 is a computed tomography image, in which a horizontal axis and a vertical axis of the center of the brain have been set in accordance with an example embodiment.

FIG. 3 is a computed tomography image on which a horizontal axis and a vertical axis of the center of the brain have been set in accordance with the example embodiment.

A method of calculating HU value according to the range of the CT numbers of each pixel of the computed tomography image may vary depending on the setting of the computed tomography image file. In addition, according to the method for densitometric analysis of the computed tomography image in accordance with the example embodiment, the range of the CT numbers of each pixel can be automatically calculated and processed through a header file.

Subsequently, referring back to FIG. 1, according to the method for densitometric analysis of a computed tomography image in accordance with the example embodiment, an artifact present in the computed tomography image can be automatically eliminated at step S200 of eliminating an artifact of a computed tomography image.

Figure 4:
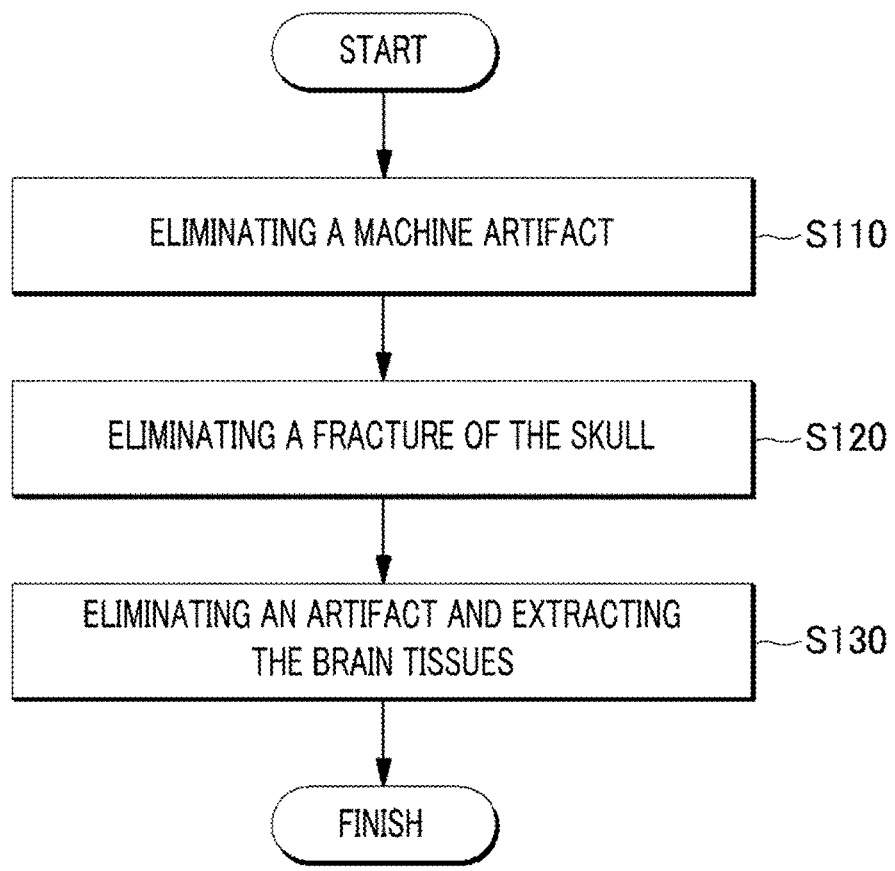
FIG. 4 is a flowchart for elaborating a process for eliminating an artifact of a computed tomography image in accordance with an example embodiment.

FIG. 4 is a flowchart for elaborating the elimination of an artifact of a computed tomography image in accordance with the example embodiment.

Referring to FIG. 4, the step S200 of eliminating an artifact in accordance with the example embodiment involves eliminating a machine artifact (S210); eliminating a fracture present in the skull (S220); and eliminating an artifact and extracting the brain tissues (S230).

According to the example embodiment, at step S210 of eliminating a machine artifact, a machine artifact present in the computed tomography image is eliminated.

In general, as a technique for acquiring a cross-sectional transverse scans of body of a subject, computed tomography (CT) is carried out within a cylindrical machine which is equipped with an X-ray generator. Specifically, the X-ray generator is positioned at one side of the subject, and an X-ray detector is provided at the other side of the subject. With this configuration, aimed X-ray beams are allowed to pass through an imaging target portion of the human body at uniform intensity from multiple different directions, and a quantity of attenuated X-ray is acquired and measured by the detector on the opposite side. Based on this measurement, a computed tomography image is constructed. In this case, each pixel constituting the computed tomography image is very critically affected by the degree of X-ray absorption. The degree of X-ray absorption is called a computer tomography scale or a Hounsfield unit (HU) named after the inventor of the computer tomography. HU value of water is 0; HU value of air is −1,000; HU value of a bone having high density is +1,000; and HU values of other materials are in the range from −1,000 to +1,000 depending on the degree of X-ray attenuation. However, HU value of a machine is very close to that of a bone. In the artifact elimination method for a computer tomography image in accordance with the example embodiment, an artifact is elimination based on HU values is performed at the last stage. As such, elimination of a machine artifact should be preceded.

The process of eliminating a machine artifact in accordance with the example embodiment are based on the features that there is an empty space between the machine and the brain in a computed tomography image, and the machine is located only at left, right and lower sides of the computed tomography image.

Figure 5:
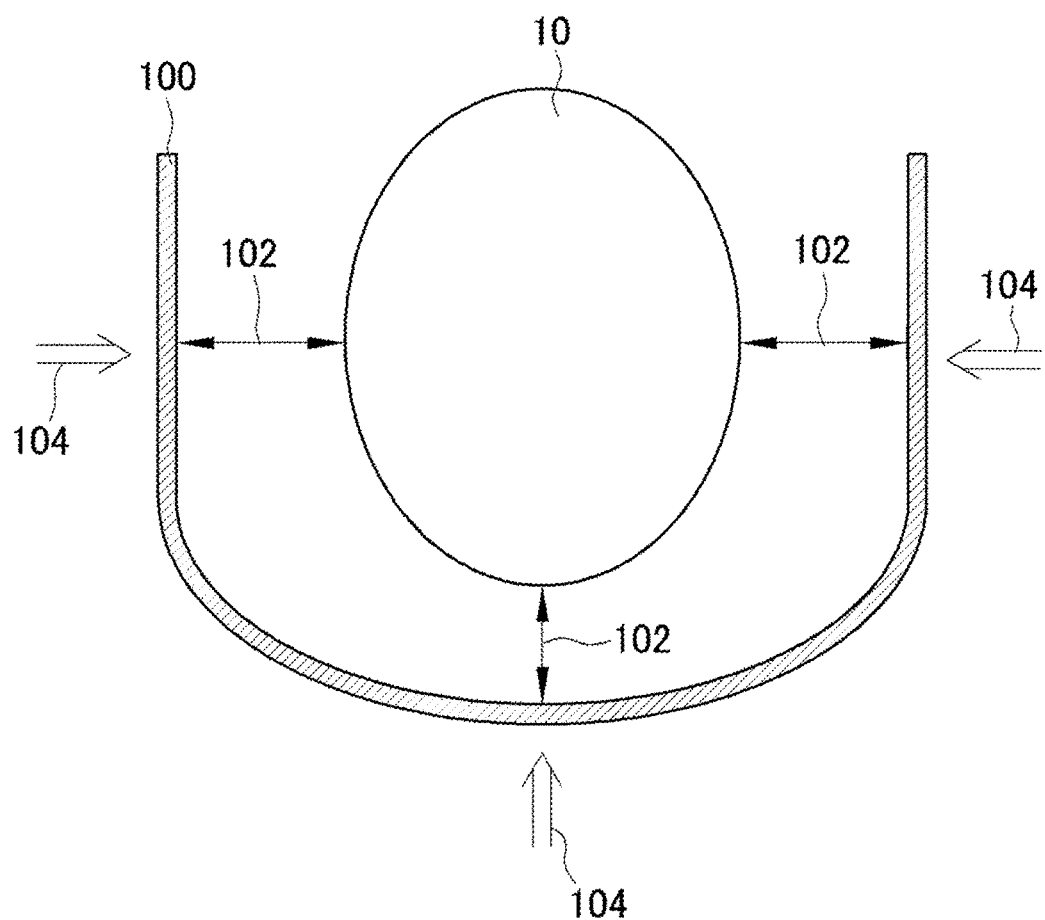
FIG. 5 is a schematic diagram of a method for eliminating a machine artifact, in the method for eliminating an artifact of a computed tomography image in accordance with an example embodiment.

FIG. 5 is a schematic diagram illustrating the method for eliminating a machine artifact, in the artifact elimination method for a computed tomography image in accordance with the example embodiment.

Figure 6:
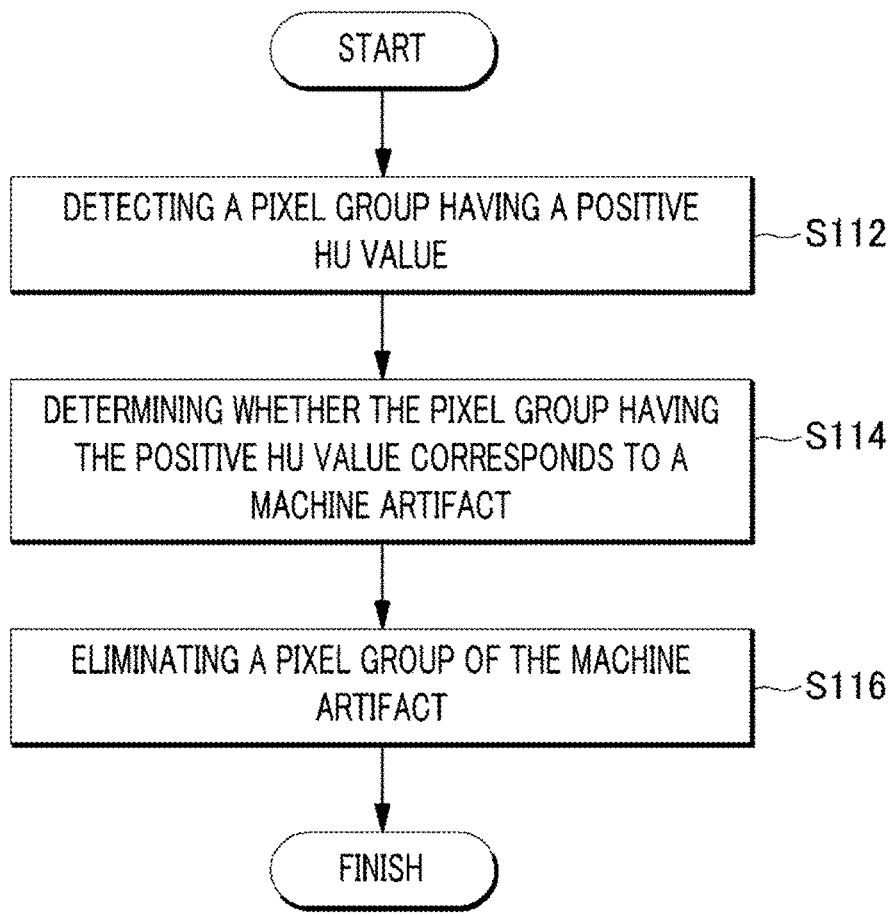
FIG. 6 is a flowchart for elaborating the process for eliminating a machine artifact in accordance with an example embodiment.

FIG. 6 is a flowchart for elaborating the process of eliminating a machine artifact in accordance with the example embodiment.

Referring to FIG. 5 and FIG. 6, the process of eliminating a machine artifact in accordance with the example embodiment includes detecting a pixel group having a positive HU value (S212); determining whether the pixel group having the positive HU value corresponds to a machine artifact (S214); and eliminating the pixel group of the machine artifact (S216).

First, at step S212 of detecting a pixel group having positive HU values, the pixel group having the positive HU values is searched by scanning the computed tomography image in the direction 104 indicated by arrows, i.e., in the direction approaching the inside of the machine from the outside of the machine.

Subsequently, at step S214 of determining whether the pixel group having the positive HU values corresponds to a machine artifact, it is determined whether or not the detected pixel group having the positive HU values corresponds to a machine artifact 100. Here, the length of a void pixel group 102 may be an important criterion for determining the machine artifact 100, and, for example, the number of void pixels may be in the range from 25 to 30.

Specifically, in the method of determining the machine artifact 100 by using the void pixel group 102 according to the example embodiment, if a series of void pixel groups 102 having negative HU values is found after the pixel group having the positive HU values is found, that pixel group having the positive HU values is determined to be the machine artifact 100.

Alternatively, assume that a computed tomography image, in which the brain 10 and the machine artifact 100 are very close to each other, is scanned in the direction 104 approaching the inside of the machine from the outside thereof. If a second pixel group having positive HU values is found after a first pixel group having positive HU values is detected, the second pixel group having the positive HU values is determined to be pixels corresponding to the brain 10, and the first pixel group is determined to be the machine artifact 100.

Next, at step S216 of eliminating the pixel group of the machine artifact, the pixel group having the positive HU values and determined to be the machine artifact 100 is eliminated.

Meanwhile, if the second pixel group having the positive HU value is not found, the machine artifact 100 may be eliminated by combining the two methods described above.

Figure 7:
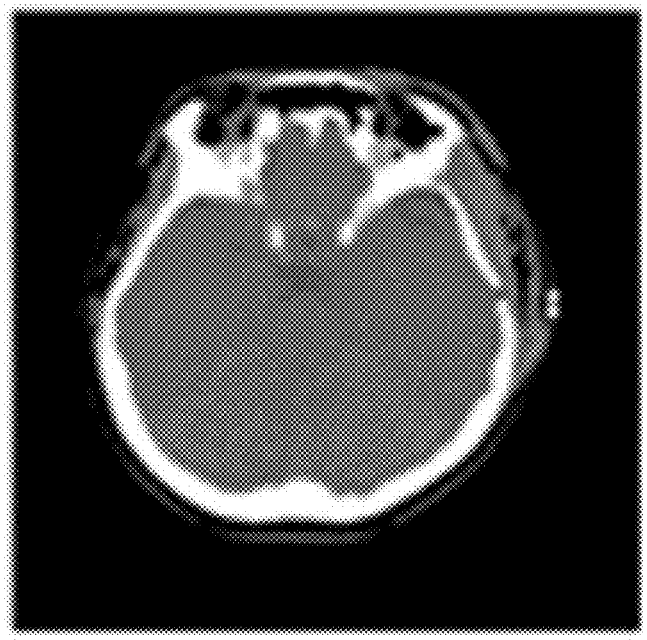
FIG. 7 is a computed tomography image, from which a machine artifact has been eliminated in accordance with an example embodiment.

FIG. 7 is a computed tomography image, from which the machine artifact has been eliminated in accordance with the example embodiment.

Referring back to FIG. 4, in the method for densitometric analysis of a computed tomography image in accordance with the example embodiment, a fracture within the skull can be eliminated after the machine artifact 100 is removed from the computed tomography image (S220).

In the densitometric analysis method for a computed tomography image in accordance with the example embodiment, fractures present in the skull of the computed tomography image are eliminated after categorized into tiny fractures and big fractures. Here, as for an example way to classify fractures of the skull into tiny fractures and big fractures, a fracture which is present in a direction parallel with X or Y axis in a computed tomography image while having a length of 20 pixels or less may be regarded as a tiny fracture. Additionally, a fracture which is present in a direction having an inclination of 1 or −1 and a length of 15 pixels or less may also be regarded as a tiny fracture. Meanwhile, if the size of a fracture is larger than the aforementioned condition for being the tiny fracture, that fracture may be regarded as a big fracture. However, such criteria for the categorization of the fractures may differ by users.

In accordance with the example embodiment, the step S220 of eliminating a fracture present in the skull of a computed tomography image may further include eliminating a tiny fracture, which is too small to be easily found, and eliminating a big fracture. First, in the process of eliminating a tiny fracture within the skull, a pixel of a fracture regarded as a tiny fracture may be replaced with a pseudo skull pixel. Here, the pseudo skull pixel means an artificial pixel having the same HU value range as that of the skull, i.e., a HU value of 80 or more. Here, when processing the tiny fracture 300, it does not matter how many fractures are processed.

Subsequently, in the process of eliminating a big fracture, a big fracture of the brain can be eliminated by finding a starting point and an end point of the fracture of the brain. Meanwhile, in the densitometric analysis method for a computed tomography image in accordance with the example embodiment, it is assumed that there exists only a single big fracture in the computed tomography image.

Figure 8:
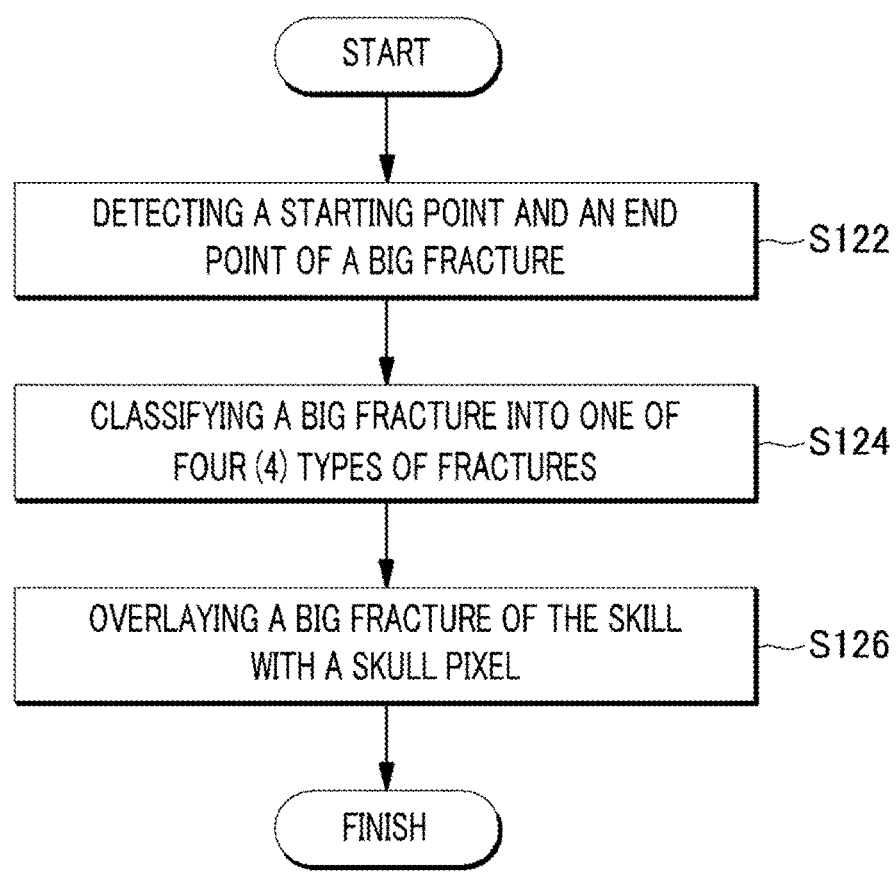
FIG. 8 is a flowchart for elaborating a method for eliminating a big fracture within the skull, in the method for densitometric analysis of a computed tomography image in accordance with an example embodiment.

FIG. 8 is a flowchart for elaborating the method of eliminating a big fracture within the skull in the densitometric analysis method for a computed tomography image in accordance with the example embodiment.

Referring to FIG. 8, the method of eliminating a big fracture within the skull in accordance with the example embodiment includes detecting a starting point and an end point of a fracture (S222); categorizing the big fracture into one of four types of fractures (S222); and overlaying the big fracture of the skull with a skull pixel (S226).

First, according to the method of eliminating a big fracture within the skull in accordance with the example embodiment, a starting point and an end point of a big fracture present within the skull are detected (S222).

In accordance with the example embodiment, each pixel of a computed tomography image has a coordinate i and a coordinate j, as a result of matrix transformation. Here, the coordinate i refers to pixels on a vertical axis, and coordinate values of the pixels increase in a downward direction on the vertical axis. Meanwhile, the coordinate j represents pixels on a horizontal axis, and coordinate values of these pixels increase in a rightward direction on the horizontal axis. However, the direction whereby the coordinate values increase or decrease may differ depending on criteria, and the present disclosure is not limited thereto.

In the densitometric analysis method for a computed tomography image in accordance with the example embodiment, top, bottom, left and right boundary points of the brain can be set by using a horizontal axis and a vertical axis of the skull on the computed tomography image in accordance with the example embodiment. Accordingly, the brain part of the computed tomography image may be divided into four split planes.

Figure 9:
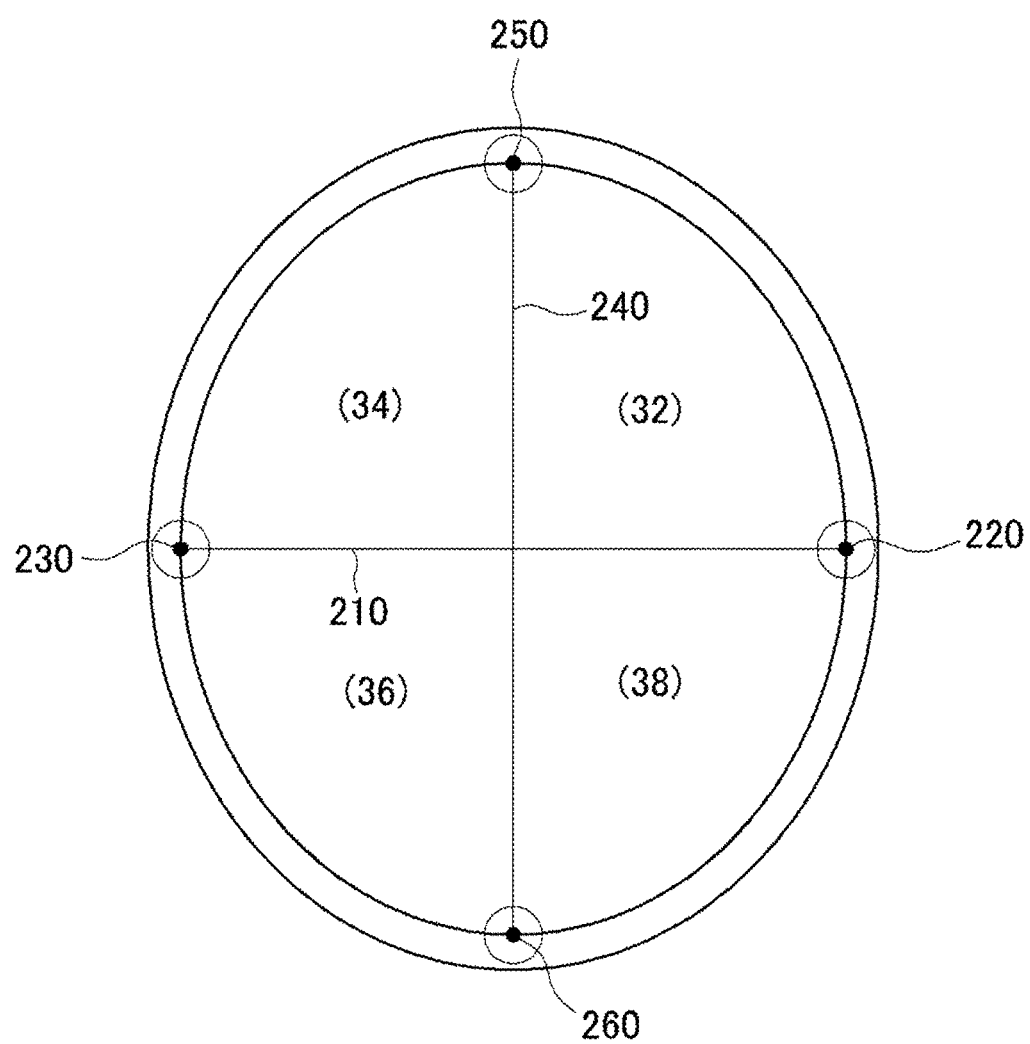
FIG. 9 illustrates setting boundary points of the brain, and dividing the brain into four (4) divided planes in accordance with an example embodiment.

FIG. 9 illustrates an example where boundary points of the brain are set and the brain is divided into four split planes in accordance with the example embodiment.

Referring to FIG. 9, in the method of setting boundary points of the brain in accordance with the example embodiment, a point on the horizontal axis of the brain which is positioned at a right edge of the brain tissues is regarded as a right boundary point 220. A point on the horizontal axis of the brain which is positioned at a left edge of the brain tissues is regarded as a left boundary point 230. In addition, a point on the vertical axis of the brain which is positioned at a top edge of the brain tissues may be set as a top boundary point 250. In addition, a point on the vertical axis which is positioned at a bottom edge of the brain tissues may be set as a bottom boundary point 260.

Subsequently, the upper right plane may be set as a first quadrant 32; the upper left plane, as a second quadrant 34; the lower left plane, as a third quadrant 34; and the lower right plane, as a fourth quadrant 38.

Next, a starting point of a fracture may be detected. The detection of the starting point of the fracture may start from the central axis of the brain, and skull pixels may be scanned in the direction whereby the value i increases. The scanning is performed from the top boundary point to the bottom boundary point. Here, a skull pixel may be used in order to find a fracture of the skull.

Figure 10:
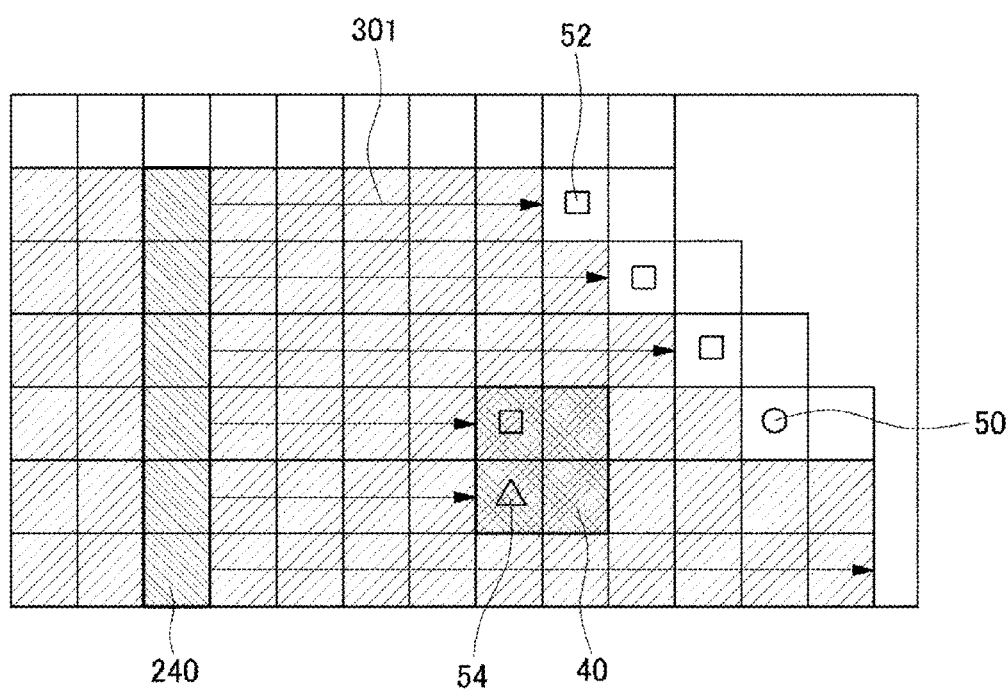
FIG. 10 illustrates a method for detecting a starting point of a fracture, in the method for densitometric analysis of a computed tomography image in accordance with an example embodiment.

FIG. 10 illustrates a method of detecting a starting point of a fracture in the densitometric analysis method for a computed tomography image in accordance with the example embodiment.

Referring to FIG. 10, according to the method of detecting a starting point of a fracture in accordance with the example embodiment, the detection may start from a pixel of the central axis 240 of the brain. For example, to detect a starting point of a fracture present on the first quadrant 32, a skull pixel 52 may be searched by scanning started from the pixel of the central axis 240 in the direction 301 in which the value j increases. Once the skull pixel 52 is found on the first line, the target line to be scanned is shifted to a line under the current line by increasing the value i, and the detection of the skull pixel 52 is then continued on this shifted line while increasing the value j once again. At this time, the skull pixel 52 may not be found on a line with a point from which a fraction starts. Accordingly, if the value j is increased to reach the right boundary point 220 of the computed tomography image but no skull pixel 52 is found, it may be considered that a fracture of the skull has been found. Then, the coordinates of the skull pixel 50 found on the previous line may be stored as a starting point of the fracture. However, when the coordinate i exceeds the bottom boundary point 260, the detection of the starting point of the fraction is terminated, and, in this case, it is concluded that no starting point of the fraction exists. Through this algorithm, since only the pixels along the skull surface are read without needing to read all brain tissue pixels, a mistake of detecting a wrong starting point of a fracture can be avoided, and the starting point of the fracture can be accurately detected.

Next, the way to detect the end point of the fracture is the same with the way to detect the starting point except that scanning is carried out in an upward direction from the bottom to the top.

In addition, detection of a big fracture is carried out on all the four split planes of the brain, and the process of detecting a starting point and an end point of a fracture on each of the second quadrant 34, the third quadrant 36 and the fourth quadrant 38 is the same with the process of detecting a fracture on the first quadrant, except for scanning directions.

At step S224 of categorizing the fracture into one of four types, the big fracture may be categorized as an upper, lower, left or right fracture. In order to categorize a fracture, it should be determined first that which quadrant of the split planes of the brain the positions of the starting and end points belong to. For example, if a starting point of a fracture is present on the first quadrant 32 and an end point of the fracture is present on the fourth quadrant 38, the fracture is categorized as a right fracture. If a starting point of a fracture is present on the second quadrant 34 and an end point thereof is present on the third quadrant 36, the fracture is categorized as a left fracture. If a starting point of a fracture is present on the second quadrant 34 and an end point thereof is present on the first quadrant 32, the fracture may be categorized as an upper fracture. If a starting point of a fracture is present on the third quadrant 36 and an end point of the fracture is present on the fourth quadrant 38, the fracture may be categorized as a lower fracture.

Next, at step S126 of overlaying of a big fracture of the skull with pseudo skull pixels, the found big fracture can be eliminated by overlaying HU value of the pixel of the found big fracture with HU value of a skull pixel or HU value of a pseudo pixel symmetrically with respect to the closed skull surface on the opposite side. For example, if either a right fracture or a left fracture is found, that fracture may be matched symmetrical to a skull line of a normal skull portion on the opposite side. Subsequently, the fracture of the skull may be eliminated by replacing the HU value of the fracture portion with the HU value of the pixel of the symmetrical skull line of the normal skull portion. Here, if a right fracture and a left fracture are found at the same time, it is deemed that there exists an upper fracture or a lower fracture, and the process of overlaying the pixels of the fracture with pseudo pixels may be omitted.

Subsequently, the presence of the upper and lower fractures is identified. If either the upper fracture or the lower fracture is found, the upper or lower fracture may be eliminated by using the normal skull line on the opposite side. In this case, since the method for eliminating the upper or lower fracture is same with the method for eliminating the right or left fracture as described above, detailed descriptions in this regard are omitted. Likewise, the process for overlaying a found fracture with skull pixels is identically applied to all the four (4) types of fractures, except for the scanning directions of the quadrants of the divided planes.

Figure 11:
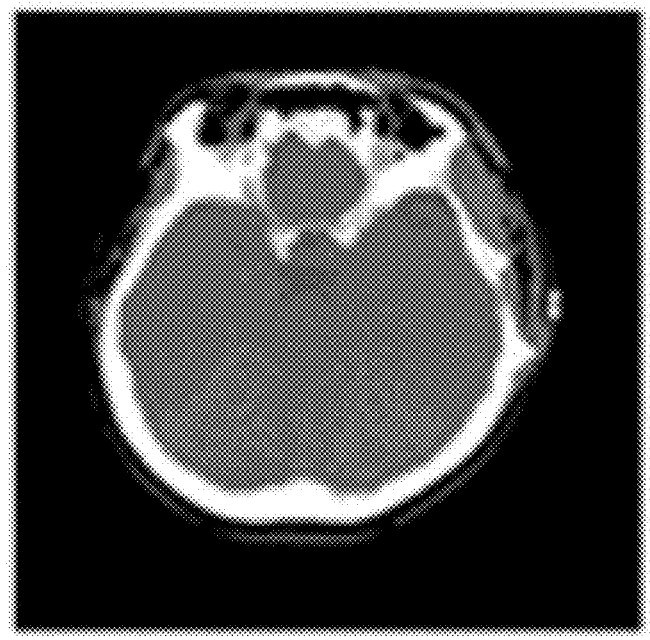
FIG. 11 shows a result of overlaying a fracture present in the skull of a computed tomography image with a pseudo skull pixel in accordance with an example embodiment.

FIG. 11 is a result of overlaying a fracture present in the skull of a computed tomography image with a pseudo pixel in accordance with the example embodiment.

Returning to FIG. 4, at step S130 of eliminating an artifact and extracting the brain tissues, all pixel values except for skull pixels are eliminated, whereby all elements outside the skull are regarded as artifacts and eliminated.

According to the densitometric analysis method for a computed tomography image in accordance with the example embodiment, the brain tissues can be solely extracted through an automatic masking process.

FIG. 12 illustrates an automatic masking process in the densitometric analysis method for a computed tomography image in accordance with the example embodiment.

Referring to FIG. 12, in order to effectively mask the brain tissues in a computed tomography image, pixels of the computed tomography image may be sorted into valid pixels corresponding to tissues and invalid pixels corresponding to the black background. Here, a standard for being an invalid CT number may be set to −1,000. In addition, a range for a valid CT number indicating tissue pixels including the eyes, the nose and the brain may be set to 79 (±)10. In accordance with the example embodiment, in the process of automatically masking tissue pixels, there may be used a four-direction valid pixel detection algorithm whereby valid pixels are searched for in four directions from a reference point.

Figure 13:
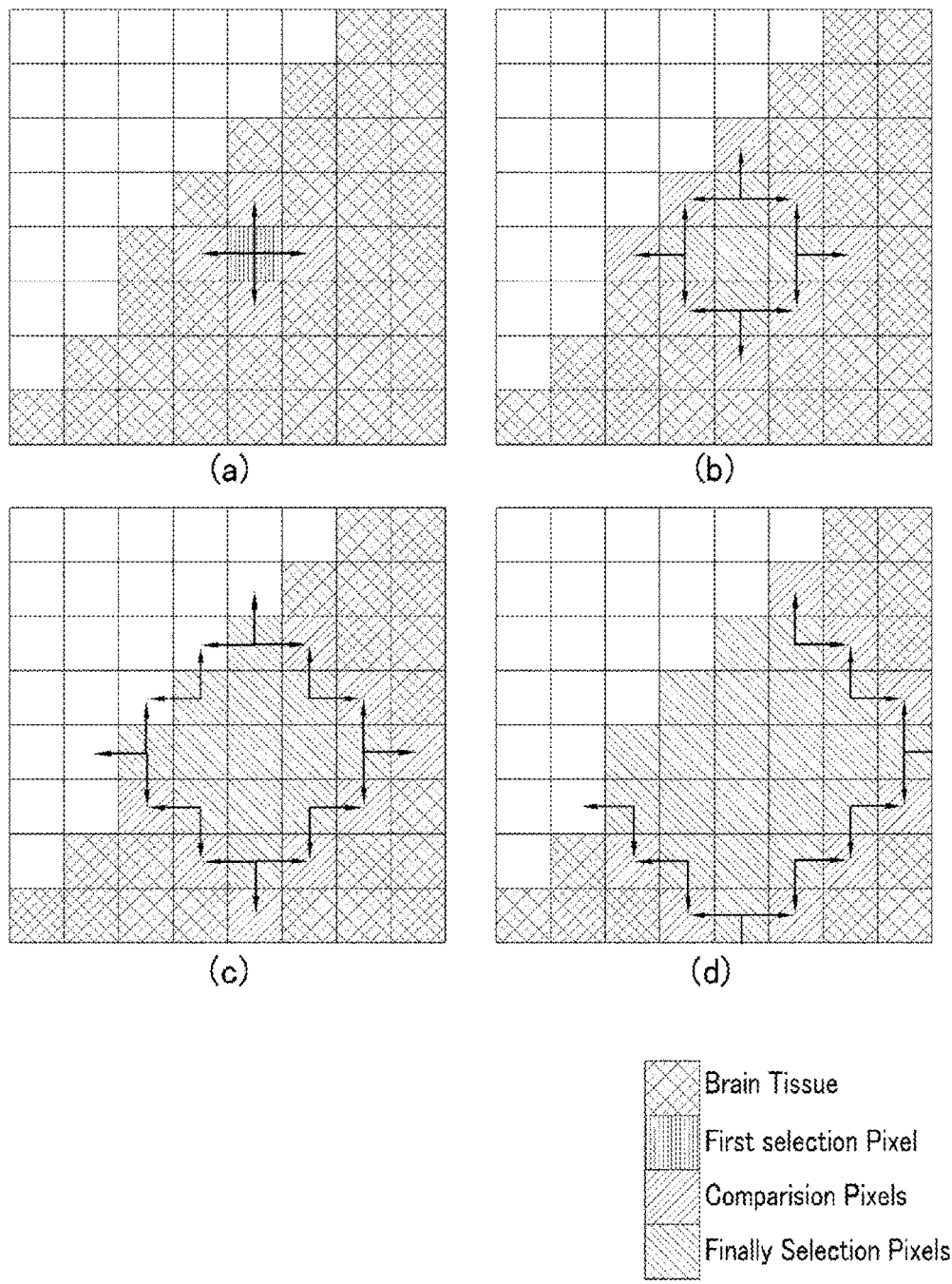
FIG. 13 is a schematic diagram for depicting a four (4)-direction valid pixel detection algorithm, in the method for densitometric analysis of a computed tomography image in accordance with an example embodiment.

FIG. 13 is a schematic diagram for elaborating the four-direction valid pixel detection algorithm in densitometric analysis method for a computed tomography image in accordance with the example embodiment.

Referring to FIG. 13, according to the four-direction valid pixel detection algorithm, CT numbers of each pixel can be scanned from a reference point pixel in four different directions, i.e., in upward, downward, leftward and rightward directions. Here, if CT number of a detected pixel value falls within the valid pixel range, the detected pixel is selected as a tissue pixel, and if the CT number of the detected pixel does not fall within the valid pixel range, the detected pixel is excluded. In this way, pixels of the tissue can be automatically masked.

In this case, the detection of valid pixels may be automatically and sequentially carried out in a total number of four directions, i.e., from a left top end point to a right bottom end point, from a right top end point to a left bottom end point, from a left bottom end point to a right top end point, and from a right bottom end point to a left top end point. Among selected tissues (the eyes, the nose, the brain and others), once a tissue having an area value of 3,000 or more is masked, the detection is stopped, and this tissue is selected and extracted as the brain tissue.

Figure 14:
FIG. 14 shows a result of extracting a tissue pixel through automatic masking, in the method for densitometric analysis of a computed tomography image in accordance with an example embodiment.

FIG. 14 is a result of extracting a tissue pixel through automatic masking in the densitometric analysis method for a computed tomography image in accordance with the example embodiment.

Meanwhile, in order to eliminate an artifact from a computed tomography image, the inside and the outside of the skull should be clearly distinguished. However, as illustrated in FIG. 14, an artifact in the form of a particle may remain outside the brain tissues, despite the artifact eliminating process described above. In this case, after the automatic masking, a process of eliminating the artifact in the particle form may be further required.

Subsequently, according to the densitometric analysis method for a computed tomography image in accordance with the example embodiment, the brain tissues, except portions of the brain under the nasal cavity and the top of the head, can be solely extracted from the computed tomography image.

Figure 15:
FIG. 15 illustrates a process of extracting the brain tissues through automatic masking, in the method for densitometric analysis of a computed tomography image in accordance with an example embodiment.

FIG. 15 illustrates a process of extracting the brain tissues through automatic masking in the densitometric analysis method for a computed tomography image in accordance with the example embodiment.

Figure 16:
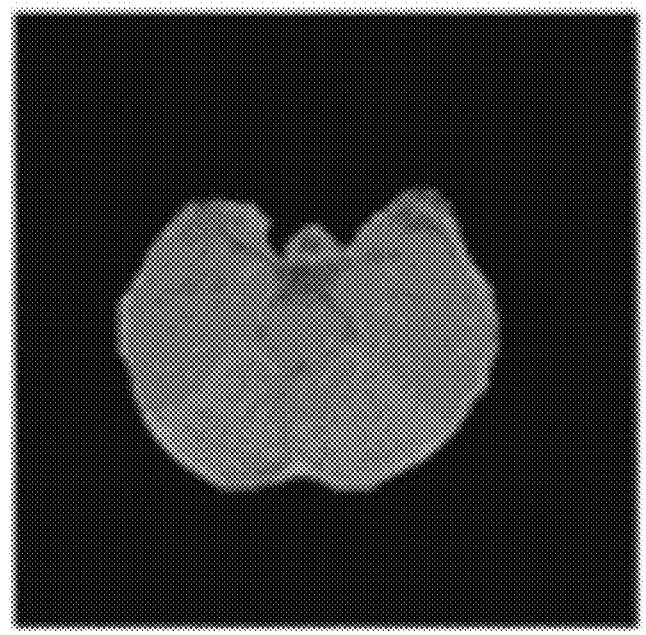
FIG. 16 is a computed tomography image, from which the brain tissues have been solely extracted by automatic masking, in the method for densitometric analysis of a computed tomography image in accordance with an example embodiment.

FIG. 16 is a computed tomography image from which the brain tissues have been solely extracted by automatic masking, in the densitometric analysis method for a computed tomography image in accordance with the example embodiment.

Referring to FIG. 15 and FIG. 16, to extract the brain tissues excluding such tissues of the eyes or the nose from a computed tomography image according to the example embodiment, a ratio between brain tissue pixels and skull pixels may be utilized. Since the portion under the nasal cavity and the top of the head are commonly characterized in that they have a far higher rate of skull pixels than that in other portions, a ratio between the brain tissue pixels and the skull pixels may be used to identify the top of the head and the portion under the nasal cavity.

For example, if the width and the length of the brain are less than 150 pixels, a reference for the ratio of the skull pixels to the brain tissue pixels may be 10:1, and if the width and the length of the brain are between 150 pixels and 250 pixels, the reference may be 5:1. In addition, if the width and the length of the brain are less than 100, the corresponding part may be regarded as the top of the head, and analysis thereof may be omitted.

Returning to FIG. 1, the densitometric analysis method for a computed tomography image in accordance with the example embodiment may extract density distribution in the computed tomography image in which an artifact has been eliminated, in the extracting of density of a mono-level computed tomography image (S300).

In accordance with an example embodiment, on a computed tomography image from which an artifact has been eliminated, pixels of the major elements within the skull, i.e., the brain tissues, the cerebrospinal fluid, the blood, etc., have certain HU values ranging from 1 to 79. Accordingly, the number of pixels having HU values ranging from 0 to 79 may be counted and stored as density unit distribution data of a mono-level computed tomography image.

Figure 18:
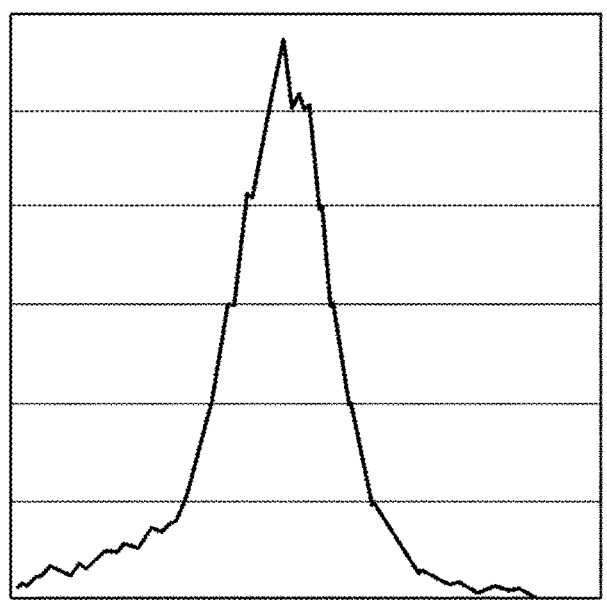
FIG. 18 is a density distribution graph for a mono-level computed tomography image, in the method for densitometric analysis of a computed tomography image in accordance with an example embodiment.

FIG. 18 is a density distribution graph of a mono-level computed tomography image, in the densitometric analysis method for a computed tomography image in accordance with the example embodiment.

In addition, the method of eliminating an artifact of a computed tomography image in accordance with the example embodiment may further include a color mapping process, after the automatic elimination of an artifact in the computed tomography image of the patient underwent craniotomy. Accordingly, it is possible to enable a user to more easily analyze a computed tomography image. At this time, the color to be mapped may vary depending on a HU value.

Figure 17:
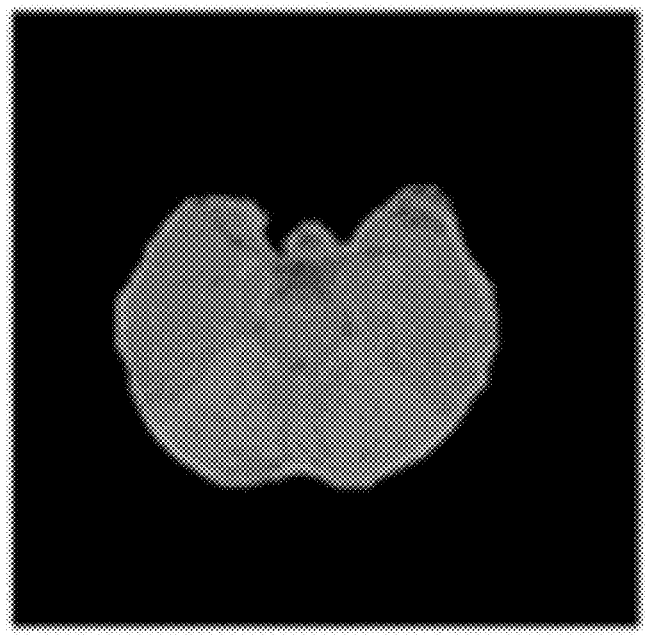
FIG. 17 is a color image of a mono-level computed tomography image obtained by the method for densitometric analysis of a computed tomography image in accordance with an example embodiment.

FIG. 17 is a color image of a mono-level computed tomography image obtained by using the densitometric analysis method for a computed tomography image according to the example embodiment.

Subsequently, referring back to FIG. 1, at step S400 of conducting a densitometric analysis for a multi-level computed tomography image, information regarding density distribution of all computed tomography images of an individual patient is collected. That is, a three-dimensional image is obtained through the color mapping process for all the computed tomography images from which artifacts have been eliminated, along with the use of the multi-level density unit distribution.

At step S400 of conducting the densitometric analysis for the multi-level computed tomography image in accordance with the example embodiment, an integrated density unit distribution can be extracted by summing up the number of pixels having each HU value in density unit distribution of all single computed tomography images, which is obtained at step S300 of extracting a density of the mono-level computed tomography image. In addition, by calculating a ratio of pixels having a certain HU value in the computed tomography image, a multi-level density unit distribution graph reflecting the whole cerebrum can be extracted.

Here, the ratio of the pixels having the certain HU value in the computed tomography image can be calculated by using following Mathematical Formula 1.

$$0 \leq \lambda \leq 79, \text{ and } \sum_{\lambda=0}^{79} p_\lambda = 100 \quad \text{[Mathematical Formula 1]}$$

Here, $p_\lambda$ denotes a ratio of the pixels having the HU values in the range from 0 to 79 within a computed tomography image, and the corresponding ratio in the computed tomography image has a percentage value in the range from 0 to 100. In addition, a sum of all $p_\lambda$ values becomes 100 according to the definition of $p_\lambda$.

For example, in case of a patient with traumatic brain injury, several computed tomography images are acquired in computer tomography examination. If n sheets of computed tomography images have been acquired, the number of pixels having $\lambda$ HU in a $k^{th}$ computed tomography image is denoted as $\lambda_c^k$. Accordingly, the number E of the pixels having the HU value of 0 to 79 in all of the computed tomography images may be represented by the following Mathematical Formula 2.

$$E = \sum_{k=1}^{n} \sum_{\lambda=0}^{79} \lambda_c^k \quad \text{[Mathematical Formula 2]}$$

Accordingly, the ratio of the pixels having the HU value of 0 to 79 within a computed tomography image is represented by the following Mathematical Formula 3.

$$p_\lambda = \frac{1}{E} \sum_{k=1}^{n} \lambda_c^k \quad \text{[Mathematical Formula 3]}$$

Here, n denotes the number of the acquired computed tomography images.

The distribution of the HU values of the brain tissues of the patient with brain injury may be acquired by calculating $p_\lambda$ for all $\lambda$. If there is a discrepancy in the distribution of HU values of certain pixels of the brain tissues of the patient with brain injury, it may mean a significant outcome indicating difference in the degree of the cerebral edema.

Returning to FIG. 1, at step S500 of conducting a batch analysis, upon the completion of the output of a three-dimensional color image through the multi-level density distribution analysis and the color mapping process for CT images of a patient, the above-described respective processes of the densitometric analysis are repeatedly performed for computed tomography images of other patients to be additionally examined.

Figure 19:
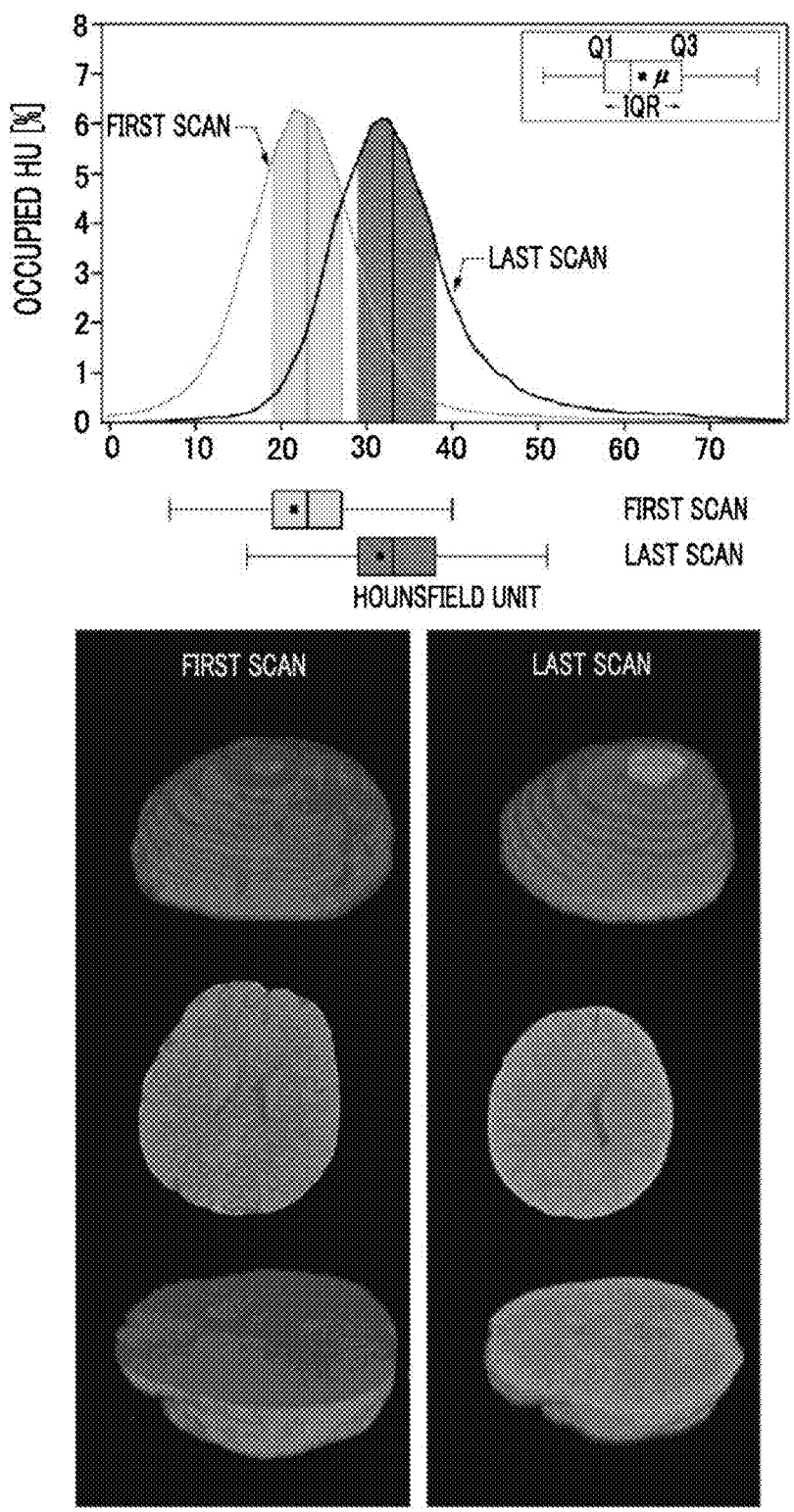
FIG. 19 shows a result of obtaining a density distribution graph of multi-level computed tomography images and a three-dimensional color image of a patient with traumatic brain injury who showed favorable outcome, through a densitometric analysis algorithm for a computed tomography image in accordance with an example embodiment.

FIG. 19 is a result of obtaining a multi-level image density distribution graph and a three-dimensional color image of a patient with traumatic brain injury who showed favorable outcome, through a densitometric analysis algorithm for a computed tomography image in accordance with the example embodiment.

Figure 20:
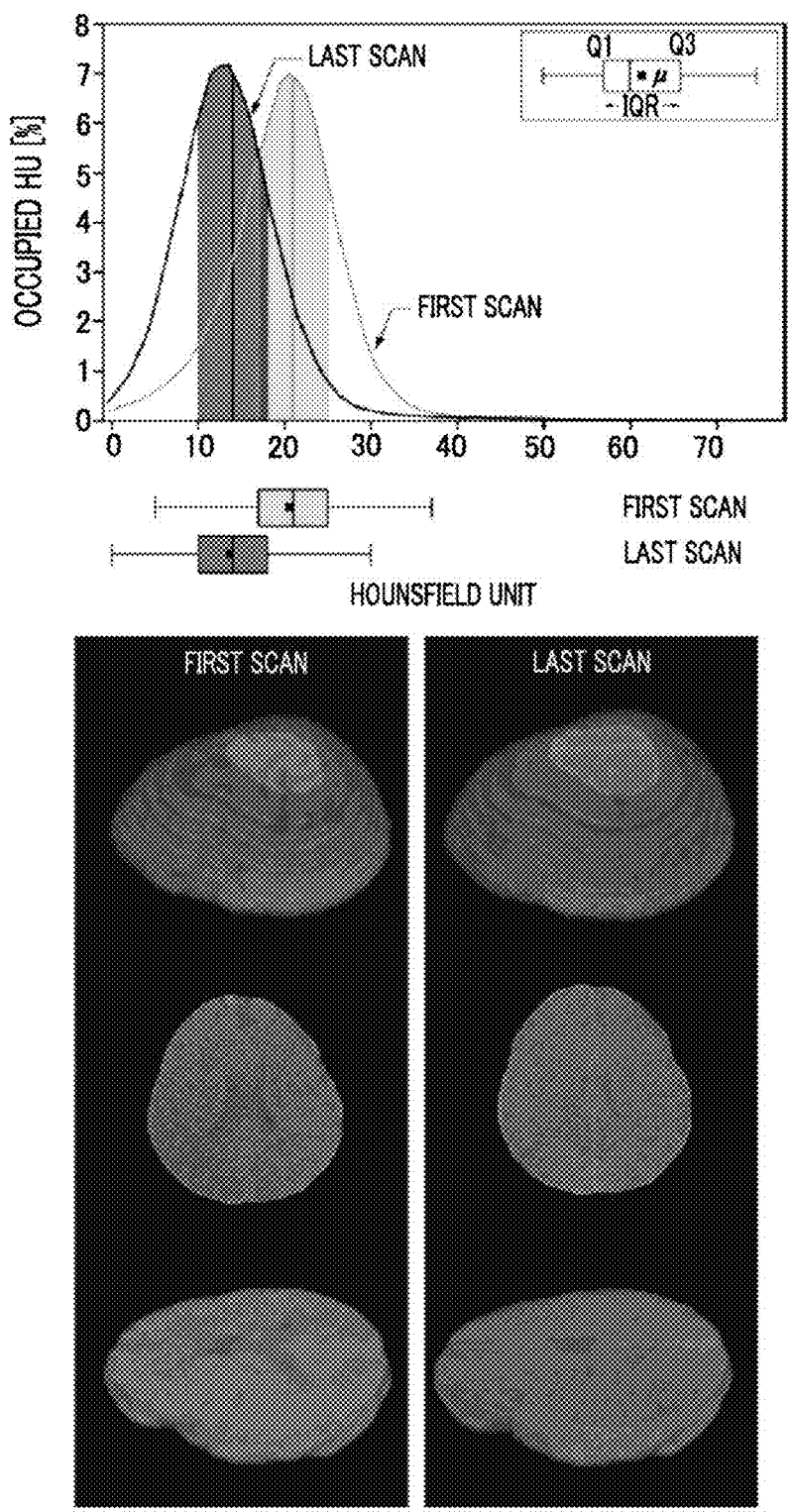
FIG. 20 is a result of obtaining a density distribution graph of multi-level computed tomography images and a three-dimensional color image of a patient with traumatic brain injury who showed unfavorable outcome, through a densitometric analysis algorithm for a computed tomography image in accordance with an example embodiment.

FIG. 20 is a result of obtaining a multi-level image density distribution graph and a three-dimensional color image of a patient with traumatic brain injury who showed unfavorable outcome, through a densitometric analysis algorithm for a computed tomography image in accordance with the example embodiment.

On the density distribution graphs of the first computed tomography scanning and the last computed tomography scanning of the patient with traumatic brain injury who showed favorable outcome and the one who showed unfavorable outcome, as illustrated in FIG. 19 and FIG. 20, gray-scale area below the distributions indicate interquartile ranges (IQR) of the density distributions. In addition, each of the density distribution graphs may be represented by a box plot below the X axis. Here, the box plot indicates a maximum value of the distribution, and a circled portion within the box plot indicates HU value occupying the highest ratio in the density distribution.

As can be seen from the density distribution graphs of FIG. 19 and FIG. 20, changes in the density distributions of the patient who showed favorable outcome and the patient who showed unfavorable outcome are significantly different. Referring to FIG. 19, in case of the traumatic brain injury patient who showed favorable outcome, it is observed that the density distribution graph of the last computed tomography image is shifted rightwards, as compared to the initial computed tomography. On the other hand, referring to FIG. 20, in case of the traumatic brain injury patient who has showed unfavorable outcome, it is found out that the density distribution graph is shifted leftwards.

As described above, according to the densitometric analysis method for a computed tomography image in accordance with the example embodiment, a shift of the density distribution according to the patient's outcome can be observed to diagnose the patient based on the computed tomography. Further, according to the densitometric analysis method of the example embodiment, changes in patterns of the density distribution graph, such as skewness reflecting the extent of asymmetry of the density distribution, kurtosis reflecting the extent of peakedness of the density distribution, a ratio of a certain HU range in the density distribution, etc. On this basis, a patient with brain injury can be examined in various different approaches.

Since Marshall classification assesses diffuse axonal injury based on user's arbitrary evaluation upon compression of basal cistern, etc., this classification system is highly user-dependent. Further, a diagnosis according to Marshall classification is made based on results caused by the diffuse axonal injury which accompanies impairment over a wide range and may not be easily identified by naked eyes. As a solution, according to the densitometric analysis method of the example embodiment, a brain injury broadly affecting the whole cerebrum can be more clearly reflected by analyzing a density distribution of multi-level HU values reflecting computed tomography images of the whole cerebrum. Accordingly, according to the densitometric analysis method for a computed tomography image in accordance with the example embodiment, it is possible to make a more exact diagnosis when examining a patient with brain injury whose prognosis is significantly affected by early detection.

In addition, the densitometric analysis method for a computed tomography image in accordance with the example embodiment suggests a densitometric Hounsfield unit score (DHS) system, which overcomes the limits of the conventional Marshall classification system and enables effective classification according to the state of a patient with traumatic brain injury. The DHS system enables automated quantitative analysis of a computed tomography image, and reflects various etiologies on the DHS formula.

The DHS formula of the densitometric analysis method in accordance with the example embodiment is defined by following Mathematical Formula 4.

$$DHS = (HU_{13}^{21} + HU_{73}^{75} + \text{lesionscore}) / HU_{28}^{33} \quad \text{[Mathematical Formula 4]}$$

Here, edema ($HU_{13}^{21}$), haemorrhage ($HU_{73}^{75}$), and normal cells ($HU_{28}^{33}$) may be obtained based on $HU_0^{79}$ distribution obtained by extracting a density distribution.

In addition, a lesion score refers to a sum of scores according to a presence or absence of a cranial fracture, infarction, brain swelling, epidural haemorrhage (EDH), subarachnoid haemorrhage (SAH), subdural haemorrhage (SDH), intracerebral haemorrhage (ICH), intraventricular haemorrhage (IVH) and others in a radiological report of a patient.

| Etiology | Count (Y/N) |
| --- | --- |
| Cranial fracture | 1 or 0 |
| Infarction | 1 or 0 |
| Brain swelling | 1 or 0 |
| Epidural haemorrhage (EDH) | 1 or 0 |
| Subarachnoid haemorrhage (SAH) | 1 or 0 |
| Subdural haemorrhage (SDH) | 1 or 0 |
| Intracerebral haemorrhage (ICH) | 1 or 0 |
| Intraventricular haemorrhage (IVH) | 1 or 0 |
| Total (lesion score) | 0~8 |

In addition, in the densitometric analysis method according to the example embodiment, the severity of the patient's state is evaluated based on a reference DHS value of the first computed tomography image, and the recovery of the patient is evaluated based on a reference DHS value of the last computed tomography image.

| Classification | | Minimum Value | Maximum Value | Average | Standard Deviation |
| --- | --- | --- | --- | --- | --- |
| Initial computed tomography image | Non-acute trauma patient | 0.05 | 2.26 | 0.3848 | 0.51595 |
| | Acute trauma patient | 0.12 | 1.34 | 0.5857 | 0.38367 |

-continued

| | Classification | Minimum Value | Maximum Value | Average | Standard Deviation |
|---|---|---|---|---|---|
| | Deceased patient | 0.31 | 7.05 | 1.8201 | 2.00352 |
| Last computed tomography image | Patient with favorable outcome | 0.05 | 2.22 | 0.3239 | 0.45459 |
| | Patient with unfavorable outcome | 0.12 | 18.22 | 2.6270 | 5.86468 |
| | Deceased patient | 0.20 | 36.83 | 5.2812 | 9.72367 |

For example, when a DHS value of the first computed tomography image is equal to or larger than 0.3848, the patient may be identified as an acute trauma patient. When a DHS value is 0.3848 or less, the patient may be identified as a non-acute trauma patient. When a DHS value is equal to or larger than 1.8201, the risk of death increases.

When a DHS value of the last computed tomography image is equal to or larger than 0.3239, the patient's outcome may be concluded as an unfavorable outcome. When a DHS value is 0.3239 or less, the patient's outcome may be identified as a favorable outcome. When a DHS value is equal to or larger than 5.2812, the patient may be found to be dead. Here, the last computed tomography image means a computed tomography image acquired after the initial computed tomography image is taken, and the outcome of the patient is evaluated based on the last image, regardless of when the last image is taken.

Meanwhile, as the DHS system suggested in the example embodiment utilizes the values calculated by quantitative analysis of computed tomography, no user-dependent variability may exist among observers. Furthermore, HU values are calculated from the whole cerebrum of each patient, and, based on this, the DHS is calculated. During this process, intervention by an observer is minimized.

In addition, the diffuse brain injury, which has not been identified by naked eyes on the computed tomography image, can be quantitatively evaluated based on a HU distribution. This approach involves investigating information regarding the entire range of density of the whole cerebrum of each patient and thus has overcome the limit of the quantitative approach of the conventionally suggested "Large Section."

Besides, DHS reflects, on the system, various eitologies, such as a cranial fracture, infarction, brain swelling, epidural haemorrhage (EDH), subarachnoid haemorrhage (SAH), subdural haemorrhage (SDH), middle line shift of intracerebral haemorrhage (ICH) and intraventricular haemorrhage (IVH), ischemia, and a mass effect. Thus, it is possible to evaluate and identify the patient's medical state accurately.

Meanwhile, an apparatus for densitometric analysis of a computed tomography image that employs the densitometric analysis method according to the example embodiment includes a storage device that stores a densitometric analysis application, and a processing unit that is arranged to interface with the densitometric analysis application. In this configuration, according to execution of the densitometric analysis application, the processing unit converts CT numbers of each pixel of a cross-sectional computed tomography scans of the brain into HU values, eliminates an artifact from the computed tomography image of which the CT numbers of each pixel have been converted into the HU values, and then, extracts a density distribution in HU values from the computed tomography image, from which an artifact has been eliminated.

The example embodiments can be embodied in a storage medium including instruction codes executable by a computer or processor such as a program module executed by the computer or processor. A computer readable medium can be any usable medium which can be accessed by the computer and includes all volatile/nonvolatile and removable/non-removable media. Further, the computer readable medium may include all computer storage and communication media. The computer storage medium includes all volatile/nonvolatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes information transmission mediums.

The above-described apparatus for densitometric analysis of a computed tomography image in accordance with the example embodiments may be realized as a computer readable code on a computer readable storage medium. The computer readable storage medium includes all kinds of storage devices storing data that can be read by a computer system. For example, there are a read only memory (ROM), a random access memory (RAM), a magnetic tape, a magnetic disk, a flash memory, an optical data storage device and others. In addition, the computer readable record medium may be distributed on a computer system connected through a computer communication network, to be stored and executed as a code that can be read in a distributed manner.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

We claim:

1. A method for densitometric analysis of a computed tomography (CT) image, comprising:
    converting CT numbers of each pixel of a cross-sectional computed tomography image of the brain into Hounsfield unit (HU) values;
    eliminating an artifact from the computed tomography image of which the CT numbers of each pixel have been converted into the HU values, and extracting the brain tissues; and
    extracting a density distribution of the HU values from the computed tomography image, in which the artifact has been removed and the brain tissues have been extracted.

2. The method for densitometric analysis of a computed tomography image as claimed in claim 1,
wherein the eliminating of an artifact comprises:
eliminating a machine artifact;
detecting a position of a fracture within the skull in the computed tomography image, in which the machine artifact has been eliminated, and overlaying a fracture region with a pseudo skull pixels; and
eliminating an artifact from the computed tomography image, which has been overlaid with the skull pixels, and extracting the brain tissues,
wherein the extracting of the brain tissues comprises categorizing each pixel of the computed tomography image into a valid pixel or an invalid pixel, setting a reference point, and searching for a valid pixel while conducting scanning in upward, downward, leftward and rightward directions, starting from the reference point.

3. The method for densitometric analysis of a computed tomography image as claimed in claim 2,
wherein the valid pixel is a pixel corresponding to a tissue in the computed tomography image and has HU value ranging from 69 to 89.

4. The method for densitometric analysis of a computed tomography image as claimed in claim 2,
wherein the invalid pixel is a pixel corresponding to the background in the computed tomography image and has HU value equal to or less than −1,000.

5. The method for densitometric analysis of a computed tomography image as claimed in claim 2,
wherein the extracting of the brain tissues further comprises
eliminating a brain portion under the nasal cavity and the top of the head, based on a ratio between a brain tissue pixel and a skull pixel.

6. The method for densitometric analysis of a computed tomography image as claimed in claim 1,
wherein the extracting of the density distribution of the HU values in the computed tomography image comprises counting and storing the number of pixels having HU values ranging from 0 or to 79.

7. The method for densitometric analysis of a computed tomography image as claimed in claim 1, further comprising:
acquiring one or more computed tomography images of the whole brain, and converting CT numbers of each pixel of the computed tomography image into HU values;
eliminating the artifact; and
repeating the extracting of the density distribution of the HU values as many times as the number of the acquired images, and
analyzing the density distribution of the HU values of the computed tomography image of the whole brain.

8. The method for densitometric analysis of a computed tomography image as claimed in claim 7,
wherein the analyzing of the density distribution of the HU values in the computed tomography image of the whole brain comprises extracting a ratio of pixels having HU values ranging from 0 to 79 from the one or more computed tomography images of the whole brain.

9. The method for densitometric analysis of a computed tomography image as claimed in claim 7, further comprising
obtaining a distribution of edema ($HU_{13}^{21}$), haemorrhage ($HU_{73}^{75}$), and normal cells ($HU_{28}^{33}$), based on the density distribution in HU values of computed tomography image of the whole brain, and
calculating a densitometric Hounsfield unit score (DHS) value of the computed tomography image, and evaluating severity of the brain lesion or improvement of the brain lesion according to the calculated DHS value,
wherein the DHS is calculated by the following:

$$DHS=(HU_{13}^{21}+HU_{73}^{75}+\text{lesionscore})/HU_{28}^{33}$$

and
a lesion score refers to a sum of scores representing a presence or absence of a cranial fracture, infarction, brain swelling, epidural haemorrhage (EDH), subarachnoid haemorrhage (SAH), subdural haemorrhage (SDH), intracerebral haemorrhage (ICH), intraventricular haemorrhage (IVH) and others in a radiological report of a patient.

10. The method for densitometric analysis of a computed tomography image as claimed in claim 9,
wherein the evaluating of the severity of the brain lesion or the improvement of the brain lesion comprises evaluating the severity of the patient's state based on a reference DHS value of the first computed tomography image, and evaluating the improvement of the patient state based on a reference DHS value of the last computed tomography image.

11. A non-transitory computer readable medium having stored thereon a program for executing the densitometric analysis method of the computed tomography image according to claim 1.

12. A method for calculating a densitometric Hounsfield unit score (DHS) from a computed tomography image, the method comprising:
(a) acquiring one or more computed tomography image of the whole brain;
(b) converting CT numbers of each pixel of the computed tomography image into HU values;
(c) eliminating an artifact from the computed tomography image of which the CT numbers of each pixel have been converted into the HU values, and extracting the brain tissues:
(d) extracting a density distribution in HU values from the computed tomography image, in which the artifact has been eliminated and the brain tissues have been extracted;
(e) analyzing the density distribution in HU values of the computed tomography image of the whole brain; and
(f) calculating a DHS value based on a distribution of edema, haemorrhage and normal cells obtained according to an analysis result of the density distribution of the HU values.

13. The method for calculating the DHS value as claimed in claim 12,
wherein processes (a) to (d) are repeated as many times as the number of acquired computed tomography images of the whole brain.

14. The method for calculating the DHS value as claimed in claim 12,
wherein the DHS is calculated by the following:

$$DHS=(HU_{13}^{21}+HU_{73}^{75}+\text{lesionscore})/HU_{28}^{33}$$

wherein $HU_{13}^{21}$ denotes a density distribution of HU values indicating edema, $HU_{73}^{75}$ denotes a density distribution of HU values indicating haemorrhage, and $HU_{28}^{33}$ denotes a density distribution of HU values indicating normal cells, and
a lesion score refers to a sum of scores according to a presence or absence of a cranial fracture, infarction, brain swelling, epidural haemorrhage (EDH), subarachnoid haemorrhage (SAH), subdural haemorrhage (SDH), intracerebral haemorrhage (ICH), intraventricular haemorrhage (IVH) and others in a radiological report of a patient.

15. The method for calculating a DHS value as claimed in claim 12, further comprising evaluating severity of the brain lesion or improvement of the brain lesion according to the calculated DHS value.

16. An apparatus for densitometric analysis of a computed tomography (CT) image, comprising:

a storage device that stores a density distribution application; and a processing unit that configured to interface with the density analysis application, wherein according to execution of the densitometric analysis application, the processing unit converts CT numbers of each pixel of a cross-sectional computed tomography image of the brain into HU values, eliminates an artifact from the computed tomography image of which the CT numbers of each pixel have been converted into the HU values, and then, extracting a density distribution in HU values from the computed tomography image, in which the artifact has been eliminated.

* * * * *